United States Patent [19]

Darsow

[11] Patent Number: 5,705,715
[45] Date of Patent: Jan. 6, 1998

[54] PROCESS FOR PREPARING 1,4-BUTANEDIOL FROM MALEIC ANHYDRIDE

[75] Inventor: Gerhard Darsow, Krefeld, Germany

[73] Assignee: Bayer Aktiengesellschaft, Leverkusen, Germany

[21] Appl. No.: 519,440

[22] Filed: Aug. 25, 1995

[30] Foreign Application Priority Data

Sep. 2, 1994 [DE] Germany .................. 44 31 220.2

[51] Int. Cl.$^6$ .................................................. C07C 31/20
[52] U.S. Cl. ........................................ 568/864; 568/861
[58] Field of Search ............................... 568/864, 861

[56] References Cited

U.S. PATENT DOCUMENTS 5,073,650  12/1991  Stabel et al. ..................... 568/864
5,196,602  3/1993   Budge et al. ..................... 568/864

FOREIGN PATENT DOCUMENTS 0447963   9/1991   European Pat. Off. .
1454440   11/1976  United Kingdom .
1587198   4/1981   United Kingdom .
03854     11/1981  WIPO .
03189     6/1986   WIPO .
8707280   12/1987  WIPO .

Primary Examiner—Marianne M. Cintins
Assistant Examiner—Dwayne C. Jones
Attorney, Agent, or Firm—Sprung Kramer Schaeffer & Briscoe

[57] ABSTRACT

Maleic anhydride (MA) is first reacted with 1,4-butanediol in a molar ratio of 1,4-butanediol:MA=1.1–2:1 to give an oligoester which is subsequently hydrogenated with excess hydrogen at 100–400 bar in two hydrogenation steps to give 1,4-butanediol. The first hydrogenation step is carried out at 60°–130° C. over a support-free catalyst of compacted metal powder of Ni, Fe, Co or mixtures thereof; the second hydrogenation step is carried out at 190°–230° C. over a reduced, support-free catalyst of compacted powders of copper oxides, ZnO and $Al_2O_3$ containing proportions of oxides of Ni, Fe, Co or mixtures of a plurality thereof. A temperature difference of 60°–130° C. is set between the two hydrogenation steps.

18 Claims, No Drawings

PROCESS FOR PREPARING 1,4-BUTANEDIOL FROM MALEIC ANHYDRIDE

BACKGROUND OF THE INVENTION

1. Field of the Invention

The present invention relates to a process for preparing 1,4-butanediol from maleic anhydride (MA), in which MA is first oligoesterified with 1,4-butanediol and the oligoester formed is hydrogenated in two hydrogenation steps over two different catalysts and in two different temperature ranges at elevated pressure and in the presence of excess hydrogen to give 1,4-butanediol.

1,4-butanediol is an important monomer or the production of thermoplastic polyesters, for example of polybutylene terephthalate PBT, and of polyurethanes having special mechanical and chemical properties, additionally an intermediate product for tetrahydrofuran and elastic fibre materials which are produced using polytetramethylene ether glycol PTMEG.

2. Description of the Related Art

It is already known that MA can be hydrogenated directly or in the form of maleic acid in aqueous solution, where, according to statements in GB 1 587 198, relatively large amounts of tetrahydrofuran and/or γ-butyrolactone are always formed in addition to 1,4-butanediol. It is also known that MA can be esterified with monoalcohols to give first a dialkyl maleate and this can be hydrogenated in a single-stage reaction zone to give a mixture of 1,4-butanediol and tetrahydrofuran, with it being possible to work in either the liquid phase (GB 1 454 440) or in the gas phase (WO 82/03854), with γ-butyrolactone being observed as intermediate. Catalysts used are copper chromite or Cu/Zn catalysts. The hydrogenation of the dialkyl maleate has also already been described in two stages (WO 86/03189), with both stages of the hydrogenation being carried out in the gas phase over copper chromite catalysts.

The processes which have become known hitherto always produce amounts of byproducts which are so large that they cause considerable expense in the purification of the reaction product. Recycling is not always possible, since the hydrogenation to give the desired end product does not always proceed smoothly and therefore leads to a relatively high level of circulated byproducts. Furthermore, a fundamental difficulty is presented by the monoalcohol used for the esterification, which alcohol fundamentally has to be separated off from the end product. The adherence to monoalcohols for the esterification is quite obviously explained by the fact that in the progressive development of the hydrogenation process from the liquid to the gaseous phase, a readily volatile ester had to be available. Another point in favour of a diester of maleic acid from monoalcohols is the fact that such esters can be reliably prepared in pure form, since contaminated starting materials generally lead to difficulties in hydrogenations.

SUMMARY OF THE INVENTION

It has now been found, contrary to this prevailing opinion, that it is possible, using the 1,4-butanediol intrinsic to the system, to prepare an oligoester which is known not to be a uniform material, and to feed this, preferably without a further pre-purification, to the hydrogenation to give 1,4-butanediol, with this hydrogenation being carried out in two hydrogenation steps over different hydrogenation catalysts and in different ranges of the hydrogenation temperature. This process has been found to be very favourable in terms of costs. It is also ecologically advantageous, since no material foreign to the system, such as a monoalcohol, is used and because only very small amounts are observed of the byproducts which usually occur and require disposal.

The invention provides a process for preparing 1,4-butanediol from maleic anhydride (MA) by esterification of the MA and catalytic hydrogenation of the ester formed in the liquid phase, which is characterized in that a) the MA is esterified using 1,4-butanediol in a molar ratio of 1,4-butanediol:MA=1.1–2:1, preferably 1.15–1.5:1, b) the esterification is carried out while distilling off the eliminated water, batchwise or continuously in 1–4 esterification stages in the temperature range of 100°–130° C., preferably 105°–125° C. and in the pressure range of 1500–100 mbar, c) the oligoester formed in step b) is treated with excess hydrogen in a first hydrogenation step in the temperature range of 60°–130° C. over a support-free catalyst of compacted metal powder of Ni, Fe, Co or mixtures thereof, and d) the hydrogenation is completed in a second hydrogenation step in the temperature range of 190°–230° C. over a reduced, support-free catalyst of compacted powders of copper oxides, ZnO and $Al_2O_3$ containing proportions of oxides of Ni, Fe, Co or mixtures of a plurality of these, with the temperature difference between the steps c) and d) being 60°–130° C., a 20 to 100-fold molar $H_2$ excess being used and the steps c) and d) being carried out at the same or different pressure in the range of 100–400 bar, preferably 150–300 bar.

DETAILED DESCRIPTION OF THE INVENTION

The course of the reaction over all steps is shown by the following reaction scheme:

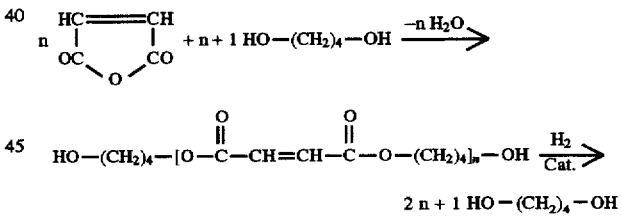

$$2n+1\ HO-(CH_2)_4-OH$$

If maleic anhydride is esterified with a monoalcohol, as is provided for in previously known processes, to obtain low-boiling dialkyl maleates, such as dimethyl maleate, diethyl maleate, dipropyl maleate, etc, it is generally necessary to carry out the reaction in the presence of an esterification catalyst and an entrainer for the water eliminated in the esterification, for example toluene. Such a process thus includes three materials foreign to the system, namely the monoalcohol, the esterification catalyst and the entrainer, which all have to be separated off at the end of the overall reaction, often even before the hydrogenation step, and worked up again. This requires a high energy consumption, because, for example, the entrainer is present in an amount many times that of the eliminated water. The purification of the dialkyl maleate prior to the catalytic hydrogenation, for example by distillation or other inconvenient methods, also requires a considerable energy consumption. After the hydrogenolytic cleavage of such a dialkyl maleate, the monoalcohol used reappears and has to be separated from the reaction products 1,4-butanediol, tetrahydrofuran and γ-butyrolactone and purified for reuse in the esterification stage. In addition, unavoidable losses have to be made up. If a monoalcohol having more than three carbon atoms is to be used for the esterification, it may be possible to omit the esterification catalyst and the entrainer. However, such higher monoalcohols are more expensive than the lower monoalcohols, so that unavoidable losses increase the costs of such a process. In addition, owing to the higher boiling points, each distillation expense is greater. In such a process, the fundamental burden of the monoalcohol, which is foreign to the system, cannot be avoided in any case.

The case is different, and advantageous, if the esterification of the MA is carried out according to the invention using 1,4-butanediol which, as a material intrinsic to the system, can remain in the reaction product. From this reaction product, a necessary amount of 1,4-butanediol can be diverted and used for the esterification of further MA. However, the 1,4-butanediol required for the esterification can, in principle, also come from another source, for example in contaminated form.

If the esterification of MA, with 1,4-butanediol is carried out at the esterification temperatures of 150°–250° C. known from the literature, the esterification in a stoichiometric mixture in a molar ratio of 1:1 remains incomplete, because there occurs, besides the esterification, as side reaction an acid-catalysed formation of tetrahydrofuran from the 1,4-butanediol used as a function of the maleic acid content which is formed as an intermediate or is initially present in the reaction mixture. Complete conversion of the MA or the maleic acid present in the reaction mixture appears to be possible only when considerable stoichiometric excesses of 1,4-butanediol are used. However, even in such a case, considerable amounts of tetrahydrofuran are still formed, for example in the esterification of 1,4-butanediol and MA in a molar ratio of 3:1 at 180° C., 15.4% by weight of tetrahydrofuran are formed as byproduct from the excess of 1,4-butanediol used.

According to the invention, the undesired formation of tetrahydrofuran can now be reduced to a value of less than 1% in the reaction mixture, if the esterification is carried out in the temperature range of 100°–130° C., preferably 105°–120° C. Permissible acid numbers in the esterification mixture, which are reached here, are 20–50 mg KOH/g. For this purpose, 1,4-butanediol and MA are reacted with one another in a molar ratio of 1.1–2:1, preferably 1.15–1.5:1. The index n given in the above reaction scheme here assumes values of 1–10, preferably 2–7, as average values, where this average comprises a distribution known per se.

The esterification is carried out in the temperature range of 100°–130° C., preferably 105°–125° C., in 1–4 esterification stages in a batchwise or continuous manner. Preference is given to carrying out the esterification in two or three esterification stages and in a continuous manner. If more than one esterification stage is being operated, it is possible, for example, to employ a plurality of esterification reactors connected in a cascade. Excessively long reaction times can be avoided by speeding up the removal of the water of reaction formed in the oligoesterification by means of fast-running stirring systems or by use of a stripping gas, for example nitrogen. In principle, it is likewise possible to use entrainers, for example toluene or similar entrainers known to those skilled in the art, to remove the eliminated water from the reaction mixture in an azeotropic distillation. However, it is an advantage of the process of the invention that such entrainers can be omitted.

The effectiveness of the esterification of the invention can advantageously be increased further if the cascade of the reactors is combined with a cascade of the reaction temperature. It has thus been found to be advantageous according to the invention to commence the esterification reaction first at as low as possible a reaction temperature within the specified range, to increase it in a further stage or in a plurality of further stages, for example from stage to stage by 5°–30° C., preferably by 5°–20° C., particularly preferably by 5°–10° C.

To accelerate the removal of the water eliminated in the esterification, it is not purposeful to work at a great superatmospheric pressure; on the contrary it is beneficial to apply reduced pressure. Therefore, the total range of 1500–100 mbar is suitable according to the invention. It is here advantageous to carry out the first esterification stage of a plurality of stages at atmospheric pressure and the last esterification stage at reduced pressure, for example at 200–500 mbar. If more than two stages are used, the intermediate esterification stages can be operated either at atmospheric pressure or at reduced pressure. An example of a combination of three esterification stages provides for atmospheric pressure in the first stage, 400–1000 mbar in the second esterification stage and 200–500 mbar in the third esterification stage.

Suitable reactors for the esterification comprise, in each case, a reaction vessel of acid-resistant material, which is equipped with an effective stirrer and a superposed distillation column of conventional construction having from 8 to 15 plates.

For use in the process of the invention, both pure MA having a purity of more than 99% and an MA containing up to 15% by weight of maleic acid are suitable. The 1,4-butanediol used advantageously also has a purity of more than 99%; but here too contents of water and/or tetrahydrofuran and/or γ-butyrolactone are permissible, as occur, for instance, in runback from distillation. A content of recycled oligomeric 1,4-butanediyl maleate is also permissible. All proportions of material foreign to the system are to be taken into account in determining the molar ratios.

The oligomeric 1,4-butanediyl maleate prepared as above is free of materials foreign to the reaction and can therefore be fed without additional purification steps directly into the subsequent hydrogenation.

The hydrogenation steps in the process of the invention are carried out in the liquid phase using excess hydrogen (20 to 100-fold molar $H_2$ excess). The liquid phase avoids the energy consumption of gas-phase processes, thus saving costs. The hydrogenation of the invention is furthermore carried out in two separate steps using different temperature ranges and different catalysts. Both catalysts are employed in the form of granular, support-free catalysts of compacted metal powder or oxide powder. This allows the reaction to be carried out in a batchwise or continuous manner, preferably in a continuous manner, avoiding the difficulties associated with pulverulent catalysts, namely the difficulty of activating pulverulent catalysts uniformly and in a targeted way, the difficulty of circulating pulverulent catalysts by means of specific slurry pumps, and the difficulty of quantitatively separating pulverulent catalysts from the reaction product. Slurry pumps are subject to a high mechanical stress. The quantitative removal of pulverulent catalysts is also complicated, because it requires a coarse filtration and a fine filtration using apparatus in exchangeable configuration. Furthermore, there is a great danger of these catalysts quickly losing their activity as a result of these additional operations, and therefore high catalyst consumptions also have to be accepted. In contrast to these indicated difficulties, the catalysts to be used according to the invention possess a high acid-insensitivity, a high pressure-insensitivity and have a high activity which does not drop even over a period of 1 or more years. The latter advantage is very important, since even in fixed-bed reactors a frequent catalyst change is very expensive.

The first hydrogenation step is carried out in the temperature range of 60°–130° C. and the second hydrogenation step is carried out at a temperature of 190°–230° C., with the temperature difference between the first and second hydrogenation steps being 60°–130° C. The pressure range for both hydrogenation steps is 100–400 bar, preferably 150–300 bar, with it being possible to carry out both hydrogenation steps at the same or different pressures within this range.

Catalysts used for the first hydrogenation step are support-free catalysts of compacted metal powder of nickel, iron, cobalt or mixtures of a plurality thereof. The term mixture here includes a mixture of powders of the individual metals and powders of previously melted binary or ternary alloys of these metals. Preference is given to using a compacted metal powder of nickel, of a mixture of nickel with iron, cobalt or iron-cobalt mixture or of a cobalt-iron mixture. If use is made of a nickel alloy or a mixture of nickel powder with powders of the other metals specified, the proportion of nickel is 60–90% by weight of the total alloy. In the case of a cobalt-iron alloy or a mixture of these metal powders, the cobalt content is 60–90% by weight of the total alloy/the total mixture. However, pure metals or alloys of pure metals are quite expensive, so that more inexpensive alternatives are sought. It has here been found that the powders of the metals or their alloys can additionally contain amounts of other metals having no catalytic action, without the high activity being reduced. The sum of the components having no catalytic action, for example Si, Al and Ti, may be up to 10% by weight of the sum of the catalytically active metals.

In the second hydrogenation step, fixed-bed catalysts used are support-free shaped bodies of pressed powders of copper oxides, zinc oxide and aluminium oxide containing proportions of oxides of nickel, iron and cobalt or mixtures of a plurality thereof. Here, the proportion of copper (calculated as metal) is 40–60% by weight, the proportion of zinc is 15–30% by weight and the proportion of aluminium is 0.2–6% by weight, based on the total amount of the compacted powder. The content of nickel, iron, cobalt or a mixture of a plurality thereof is 0.1–1% by weight, preferably 0.2–0.5% by weight, all calculated as metal. Alkali and alkaline earth metals may be present in an amount of up to 0.1% by weight. The remainder making up 100% by weight is oxygen for the metals present in oxidic form.

The support-free shaped bodies can be produced by customary methods by pressing the metal powder or metal oxide powder, for example on tabletting or pelletizing machines, under high pressure, with graphite and/or adhesives also being able to be used in amounts of 0.5–1% by weight, based on the total weight of the constituents to be compacted, to improve the adhesion of the metal particles or metal oxide particles. The production and storage of the support-free shaped bodies of compacted metal powders is preferably carried out in an oxygen-free atmosphere, to avoid surface oxidation. Examples of shaped bodies for both hydrogenation steps are pellets, spheres or granules having diameters of 3–7 mm. Pelletized shaped bodies can furthermore be provided with an axial hole to increase the external surface area. Looked at macroscopically, such shaped bodies have a smooth surface. The compacted shaped bodies used in both hydrogenation steps have a high compressive strength on the surface of the shaped body. The compacted metal powders used in the first hydrogenation step have a compressive strength of 50–500N, preferably 100–400N on the vaulted surface of the shaped body. The compacted metal oxide powders used in the second reactor have a compressive strength of 50–200N, preferably 75–150N on the vaulted surface of the shaped body. The internal surface area of the compacted metal powders for the first hydrogenation step is 10–90 m$^2$/g. The internal surface area of the compacted metal oxide powders used in the second hydrogenation step is 30–80 m$^2$/g. The compressive strength of the support-free shaped bodies can be determined in accordance with DIN 50 106. The determination of the internal surface areas is carried out in accordance with F. M. Nelson and F. T. Eggertsen, Analyt. Chem. 30 (1958), 1387 or S. J. Gregg and S. W. Sing, Adsorption, Surface Area and Porosity, London 1967, Chapter 2 and 8.

While there is in principle no difference between allowing the 1,4-butanediyl maleate to flow from the bottom upwards or from the top downwards in the vertically positioned hydrogenation reactors and independently of one another in the two hydrogenation reactors, it has been found to be advantageous to move the oligomeric 1,4-butanediyl maleate rising from the bottom upwards in the first reactor and descending from the top downwards in the second reactor, i.e. as a trickling phase. Here, the 1,4-butanediyl maleate to be hydrogenated can either be allowed to flow over the catalyst together with the previously mixed in hydrogen (cocurrent process) or the 1,4-butanediyl maleate can be conducted counter to the flow of hydrogen (countercurrent process).

The hydrogenation reactors can be individual high-pressure tubes of steel or a steel alloy which are completely or partially filled with the shaped bodies, with the use of the support-free shaped bodies on racks (for instance wire baskets or the like) also being able to be useful for relatively large tube cross-sections; however, it is also possible to use high-pressure tube bundles within a common shell, with the individual tubes again being able to be completely or partially filled with the support-free shaped bodies.

While the shaped bodies of compacted metal powders used in the first hydrogenation stage are used without further activation, the shaped bodies of compacted oxide powders used as catalysts in the second reactor have to be carefully reduced prior to use. This is achieved by use of a reduction gas comprising an inert gas/hydrogen mixture in which the hydrogen content is initially 10–15% by volume. The inert gas used is preferably nitrogen. The reduction is carried out, for example, over a period of about 24 hours at a reduction temperature of 180°–200° C., with the nitrogen content of the gas mixture being steadily decreased in the final phase of the reduction, until finally pure hydrogen flows through the reactor for the purpose of the reduction. The reduction is complete when the catalyst no longer consumes any hydrogen and as a consequence no further water of reaction is formed.

The weight hourly space velocity over the hydrogenation catalyst can be 200–400 g of 1,4-butanediyl maleate per liter of catalyst in both hydrogenation stages. High catalyst operating lives of 12,000–16,000 hours can be achieved using the process of the invention.

The reaction mixture leaving the second hydrogenation stage comprises, after decompression in which the excess hydrogen can be collected and reused after compression and making up of the hydrogen consumed, 97% by weight or more of 1,4-butanediol. It contains as organic low boilers, besides a maximum of 0.5% by weight of tetrahydrofuran, a maximum of 0.1% by weight of n-butanol and a maximum of 0.4% by weight of γ-butyrolactone, and also subordinate amounts of higher boilers of a maximum of 1.0% by weight of a relatively high molecular weight residue, and also a maximum of 1.0% by weight of $H_2O$. γ-Butyrolactone and higher boilers are returned to the process, so that the total selectivity thereof in respect of 1,4-butanediol is above 98% by weight.

After the distillative removal of low and high boilers, the 1,4-butanediol produced is obtained in a purity of above 99.8% by weight and, in this purity, can be used for all further chemical processes.

EXAMPLES

Example 1

A solution of 768 g (7.83 mol) of maleic anhydride (MA) in 1059 g (11.75 mol) of 1,4-butanediol was placed in the first reactor of a reactor cascade made of acid-resistant material, which cascade comprised 3 reactors connected in series each having a volume of 5 l and each being provided with a high-speed stirring system of conventional construction (turbine stirrer, speed: 800–1200/min) and a distillation column (10 theoretical plates), the solution was quickly heated while stirring to a reaction temperature of 105°–100° C. and the water of reaction which formed was distilled off. After a reaction time of 6 hours, the reaction mixture was transferred into the connected second reactor; there a further part of the water of reaction was distilled off at a reaction temperature of 110°–115° C. while stirring. After a reaction time of 4 hours, the reaction mixture was finally transferred into the connected third reactor; there the remainder of the water of reaction was removed under a pressure of 400 mbar and at a reaction temperature which was gradually increased from 115° to 125° C. After a further 2 hours (total of 12 hours), the esterification was ended. The oligomeric 1,4-butanediyl maleate obtained (1682 g) had a mean degree of oligomerization of n=3 (measured by gel permeation chromatography) and an acid number of 21 mg KOH/g of reaction mixture.

Directly after emptying the first reactor, the esterification process can be started again and carried on continuously in the same way.

Example 2

A solution of 899 g (9.17 mol) of MA in 950 g (10.5 mol) of 1,4-butanediol was placed in the first reactor of the same reactor cascade as in Example 1, the solution was heated while stirring to a reaction temperature of 105°–110° C. and the water of reaction which formed was distilled off. After a reaction time of 8 hours, the reaction mixture was drained into the connected second reactor; there a further part of the water of reaction was distilled off at a reaction temperature of 110°–115° C. After a reaction time of 2 hours, the reaction mixture was finally drained into the third reactor; there the remainder of the water of reaction was removed under a pressure of 350 mbar and at a reaction temperature of 115°–120° C. After a reaction time of a further 2 hours (total of 12 hours), the esterification had ended. The oligomeric 1,4-butanediyl maleate obtained (1684 g) had a mean degree of oligomerization of n=5 (molecular weight distribution measured by gel permeation chromatography) and an acid number of 42 mg KOH/g of reaction mixture.

Example 3

A vertically positioned, heat-insulated high-pressure tube made of stainless, acid-resistant steel and having an internal diameter of 45 mm and a length of 1 m, which tube had previously been flushed free of oxygen by means of nitrogen, was charged with 1.4 l of a hydrogenation catalyst produced by pelletizing a pulverized nickel-iron alloy. The alloy contained a proportion of iron in nickel of 15% by weight. The pellets had a cylinder height of 5 mm and a diameter of 5 mm, a compressive strength of 132N on the cylindrical surface and an internal surface area of 81 $m^2/g$.

Downstream of this first high-pressure tube there was connected, via a strong high-pressure line which was conducted via an electrically heatable heat exchanger, a second vertically positioned, heat-insulated high-pressure tube made of stainless, acid-resistant steel and having an internal diameter of 45 mm and a length of 1 m, this second tube having been charged with 1.4 l of a hydrogenation catalyst produced by pelletizing powders of copper, zinc, aluminium and iron oxides. The copper content of the pellets was 43% by weight, the zinc content was 16% by weight, the aluminium content was 2.2% by weight and the iron content was 0.25% by weight (remainder: oxygen). The pellets had a cylinder height of 5 mm and a diameter of 5 mm, a compressive strength of 120N on the cylindrical surface and an internal surface area of 72 $m^2/g$.

To activate the catalyst containing a mixture of metal oxides, the pellets were first dried for 6 hours in a stream of nitrogen (temperature: max. 200° C., flow: 5 standard $m^3$ of $N_2/h$). The actual activation was carried out under a nitrogen pressure of 200 bar at a temperature between 180° and 200° C., with hydrogen being gradually mixed into the inert gas, the proportion of hydrogen added not being allowed to exceed 10–15% by volume in the initial phase. Over a period of 24 hours, the proportion of nitrogen in the gas mixture was steadily decreased until finally pure hydrogen flowed through the reactor. The reaction had ended when no more water of reaction, which was collected in a downstream separator, was formed.

After activation of the hydrogenation catalyst containing a mixture of metal oxides, the inert gas nitrogen present in the first hydrogenation reactor was replaced by pure hydrogen and the hydrogen pressure in the two reactor systems which were linked to one another in such a way that the 1,4-butanediyl maleate to be hydrogenated had to pass through the first high-pressure tube ascending from the bottom upwards and through the second high-pressure tube descending from the top downwards, was increased to 250 bar.

Subsequently, 420 g/h of 1,4-butanediyl maleate, which had been obtained according to Example 1, were pumped together with 5 standard $m^3$ of hydrogen under a pressure of 250 bar through the high-pressure tubes connected in series, with the 1,4-butanediyl maleate being heated to a temperature of 110° C. in an upstream electrically heated heat exchanger prior to entry into the first high-pressure tube; the reaction product leaving the first high-pressure tube was heated to 210° C. prior to entry into the second high-pressure tube.

The reaction product (crude 1,4-butanediol) leaving the second reaction tube was cooled in a third heat exchanger (water cooler) under 250 bar hydrogen pressure to a temperature <60° C. and separated in a gas separator from excess hydrogen which was recirculated to the hydrogenation system.

After further cooling to a temperature of <30° C. and decompression to atmospheric pressure, the reaction product was analysed by gas chromatography.

It contained as organic low boilers 0.4% by weight of tetrahydrofuran, 0.5% by weight of n-butanol and 0.3% by weight of γ-butyrolactone, and as high boilers 0.4% by weight of unreacted 1,4-butanediyl maleate, so that the 1,4-butanediol content of the organic reaction product was 98.85% by weight.

The 1,4-butanediol produced was obtained in a purity of 99.9% by weight after the distillative removal of low and high boilers.

Since both the γ-butyrolactone and the unreacted 1,4-butanediyl maleate were able to be recycled to the process, the total selectivity of the process in respect of 1,4-butanediol was 99.55% by weight.

After a running time of 4600 hours, the catalysts had unchanged activity, so that the composition of the reaction product did not change over this period of time.

Example 4

A high-pressure tube as in Example 3 was charged under inert gas with 1.4 l of a hydrogenation catalyst produced by pelletizing nickel powder which additionally had an aluminium content of 5.8% by weight as binder. The pellets had a cylinder height of 3 mm and a diameter of 3 mm, a compressive strength of 147N on the cylindrical surface and an internal surface area of 33 m²/g.

Downstream of the first high-pressure tube there was connected a second high-pressure tube as in Example 3 which had been charged with 1.4 l of a hydrogenation catalyst produced by pelletizing powders of copper, zinc, aluminium and nickel oxides. The copper content of the pellets was 51% by weight, the zinc content was 27% by weight, the aluminium content was 0.5% by weight and the nickel content was 0.25% by weight (remainder: oxygen). The pellets had a cylinder height of 3 mm and a diameter of 3 mm, a compressive strength of 75N on the cylindrical surface and an internal surface area of 35 m²/g.

After the activation of the hydrogenation catalyst containing a mixture of metal oxides, as in Example 3, the inert gas nitrogen present in the first hydrogenation reactor was replaced by pure hydrogen and the hydrogen pressure in both reaction systems, which were linked to one another in the same way as in Example 3, was increased to 300 bar.

Subsequently, 560 g/h of 1,4-butanediyl maleate, which had been obtained according to Example 2, was continuously pumped together with 5 standard m³ of hydrogen under a pressure of 300 bar through the high-pressure tubes connected in series, with the 1,4-butanediyl maleate being heated to a temperature of 100° C. prior to entry into the first high-pressure tube and the reaction product leaving the first high-pressure tube being heated to 200° C. prior to entry into the second high-pressure tube.

The reaction product (crude 1,4-butanediol) leaving the second reaction tube contained, after separating off excess hydrogen and cooling to a temperature of <30° C., as organic low boilers 0.45% by weight of tetrahydrofuran, 0.07% by weight of n-butanediol and 0.4% by weight of γ-butyrolactone and as high boilers 0.35% by weight of unreacted 1,4-butanediyl maleate according to analysis by gas chromatography, so that the 1,4-butanediol content of the organic reaction product was 98.73% by weight.

After the distillative removal of low and high boilers, the 1,4-butanediol produced was obtained in a purity of 99.9% by weight.

Since both the γ-butyrolactone and the unreacted 1,4-butanediyl maleate were able to be recycled to the process, the total selectivity of the process in respect of 1,4-butanediol was 99.48% by weight.

After a running time of 5800 hours, the catalysts had unchanged activity, so that the composition of the reaction product did not change over this period of time.

Example 5

A high-pressure tube as in Example 3 was charged under inert gas with 1.4 l of a hydrogenation catalyst produced by pelletizing a pulverized nickel-cobalt alloy. The alloy contained a proportion of cobalt in nickel of 10% by weight. The pellets had a cylinder height of 5 mm and a diameter of 5 mm, a compressive strength of 187N on the cylindrical surface and an internal surface area of 68 m²/g.

Downstream of the first high-pressure tube there was connected a second high-pressure tube as in Example 3 which had been charged with 1.4 l of a hydrogenation catalyst produced by pelletizing powders of copper, zinc, aluminium and cobalt oxides. The copper content of the pellets was 49% by weight, the zinc content was 29% by weight, the aluminium content was 1.3% by weight and the cobalt content was 0.22% by weight. The pellets had a cylinder height of 5 mm and a diameter of 5 mm, a compressive strength of 108N on the cylindrical surface and an internal surface area of 49 m²/g.

After the activation of the oxidic hydrogenation catalyst as in Example 3, the inert gas nitrogen present in the first hydrogenation reactor was replaced by pure hydrogen and the hydrogen pressure in both reaction systems, which were linked to one another in the same way as in Example 3, was increased to 300 bar.

Subsequently, 420 g/h of 1,4-butanediyl maleate, which had been obtained according to Example 1, was continuously pumped together with 5 standard m³ of hydrogen under a pressure of 300 bar through the high-pressure tubes connected in series, with the 1,4-butanediyl maleate being heated to a temperature of 120° C. prior to entry into the first high-pressure tube and the reaction product leaving the first high-pressure tube being heated to 220° C. prior to entry into the second high-pressure tube.

The reaction product (crude 1,4-butanediol) leaving the second reaction tube contained, after separating off excess hydrogen and cooling to a temperature of <30° C., as organic low boilers 0.48% by weight of tetrahydrofuran, 0.09% by weight of n-butanol and 0.45% by weight of γ-butyrolactone and as high boilers 0.48% by weight of unreacted 1,4-butanediyl maleate according to analysis by gas chromatography, so that the 1,4-butanediol content of the organic reaction product was 98.50% by weight.

Since both the γ-butryolactone and the unreacted 1,4-butanediyl maleate were able to be recycled to the process, the total selectivity of the process in respect of 1,4-butanediol was 99.43% by weight.

After a running time of 3600 hours, the catalysts had unchanged activity, so that the composition of the reaction product did not change over this period of time.

What is claimed is:

1. A process for preparing 1,4-butanediol from maleic anhydride (MA) by esterification of the MA and catalytic hydrogenation of the ester formed in the liquid phase, wherein
   a) the MA is esterified using 1,4-butanediol in a molar ratio of 1,4-butanediol:MA=1.1–2:1,
   b) the esterification is carried out while distilling off the eliminated water, batchwise or continuously in 1–4 esterification stages in the temperature range of 100°–130° C. and in the pressure range of 1500–100 mbar, c) the oligoester formed in step b) is treated with excess hydrogen in a first hydrogenation step in the temperature range of 60°–130° C. over a support-free catalyst of compacted metal powder of Ni, Fe, Co or mixtures thereof, and d) the hydrogenation is completed in a second hydrogenation step in the temperature range of 190°–230° C. over a reduced, support-free catalyst of compacted powders of copper oxides, ZnO and $Al_2O_3$ containing proportions of oxides of Ni, Fe, Co or mixtures of a plurality of these, with the temperature difference between the steps c) and d) being 60°–130° C., a 20 to 100-fold molar $H_2$ excess being used and the steps c) and d) being carried out at the same or different pressure in the range of 100–400 bar.

2. The process of claim 1, wherein the molar ratio of 1,4-butanediol:MA is 1.15–1.5:1.

3. The process of claim 1, wherein the temperature range in step b) is 105°–125° C.

4. The process of claim 1, wherein the steps c) and d) are carried out at the same or different pressure in the range of 150–300 bar.

5. The process of claim 1, wherein in multistage esterification the temperature rises from stage to stage by 5°–30° C.

6. The process of claim 5, wherein the temperature rises from stage to stage by 5°–20° C.

7. The process of claim 6, wherein the temperature rises from stage to stage by 5°–10° C.

8. The process of claim 1, wherein the esterification is carried out continuously in two or three esterification stages.

9. The process of claim 8, wherein the first esterification stage is carried out at atmospheric pressure, the last esterification stage is carried out at 200–500 mbar and, in the case of three esterification stages, the middle esterification stage is carried out at 400–1000 mbar.

10. The process of claim 1, wherein the catalyst used for the first hydrogenation stage is a compacted metal powder of Ni, of a mixture of Ni with Fe, Co or Fe—Co mixture having an Ni content of 60–90% by weight of the total alloy or of a Co—Fe alloy having a Co content of 60–90% by weight of the total alloy.

11. The process of claim 1, wherein the catalyst of compacted metal powder used in the first hydrogenation step has a compressive strength of 50–500N on the vaulted surface of the shaped body and an internal surface area of 10–90 $m^2/g$.

12. The process of claim 11, wherein the catalyst has a compressive strength of 100–400N.

13. The process of claim 1, wherein the catalyst used for the second hydrogenation stage is a compacted mixture of metal oxide powders whose Cu content is 40–60% by weight, whose Zn content is 15–30% by weight, whose Al content is 0.2–6% by weight and whose content of Ni, Fe, Co or a mixture of a plurality thereof is 0.1–1% by weight with all percentages being based on the total amount of oxide powder and the remainder to 100% by weight being oxygen.

14. The process of claim 13, wherein the catalyst has a content of Ni, Fe, Co or a mixture of a plurality thereof of 0.2–0.5% by weight based on the total amount of oxide powder.

15. The process of claim 1, wherein the catalyst of compacted metal oxide powders used in the second hydrogenation step has a compressive strength of 50–200N on the vaulted surface of the shaped body and an internal surface area of 30–80 $m^2/g$.

16. The process of claim 15, wherein the catalyst has a compressive strength of 75–150N.

17. The process of claim 1, wherein the oligoester formed in step b) is used without purification for the hydrogenation.

18. The process of claim 1, wherein the catalyst for the second hydrogenation step d) is reduced at 180°–200° C. by an inert gas/hydrogen mixture prior to its use.

* * * * *